US00PP10802P

United States Patent [19]

Egger et al.

[11] Patent Number: Plant 10,802

[45] Date of Patent: Feb. 23, 1999

[54] ASIATIC HYBRID LILY PLANT NAMED 'PINK PAGODA'

[75] Inventors: Donald L. Egger, Wilsonville; Teresa Pankiewicz-Leap, Portland, both of Oreg.

[73] Assignee: Cebeco Lilies, Inc., Aurora, Oreg.

[21] Appl. No.: 918,052

[22] Filed: Aug. 25, 1997

[51] Int. Cl.[6] ..... A01H 5/00

[52] U.S. Cl. ..... Plt./87.4

[58] Field of Search ..... Plt./87.4

[56] References Cited

U.S. PATENT DOCUMENTS

P.P. 7,631 8/1991 Veenstra ..... Plt./87.4

*Primary Examiner*—Howard J. Locker

*Attorney, Agent, or Firm*—Klarquist Sparkman Campbell Leigh & Whintson, LLP

[57] ABSTRACT

A new and distinct Asiatic Lily Hybrid for the garden having upright, multicolored flowers which form a striking pattern of pink to red-purple with a light eye and maroon brush-marks and spots.

2 Drawing Sheets

BACKGROUND OF THE INVENTION

The present invention relates to a new and distinct cultivar of Lily hybrid referred to commercially as an upright Asiatic hybrid lily and given a cultivar name of 'Pink Pagoda'. This invention was developed by controlled breeding in Aurora, Oreg., using A-001-85, 'Tamara', as the seed parent and A-090-82, 'Beaudacious', U.S. Plant Pat. No. 7,631 as the pollen parent.

This invention has not been observed under all possible environmental conditions. The phenotype may vary significantly with variations in environment such as temperature, light intensity and day length, without, however, any variation in genotype.

The following traits have been repeatedly observed and are determined to be the basic characteristics of this invention which in combination distinguish this lily as a new and distinct cultivar: 1) strikingly patterned and multicolored flowers of light orange to pink to red-purple with a dark maroon brushmark; 2) multicolored pink, yellow-green, and red-purple buds; 3) early bloom time; and 4) good disease tolerance.

Of the many cultivars known to the inventor, the inventor is not aware of any other Asiatic lily commercially available with the unique color and striking pattern of this invention.

Asexual reproduction of this new variety has been accomplished at Cebeco Lilies, Inc., Aurora, Oreg. by scaling and tissue culture. The resulting plants have shown that the above-mentioned unique features are stable and reproduce true to type in each successive propagation.

Figure 1:
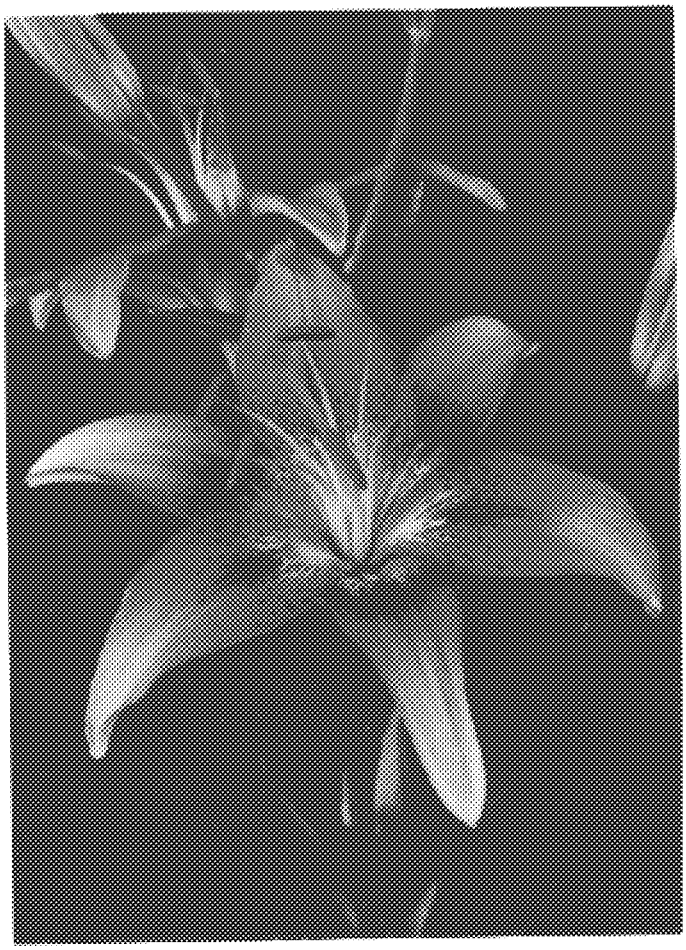
FIG 1. is a close-up photograph which illustrates in detail a single flower of the new plant.
Figure 2:
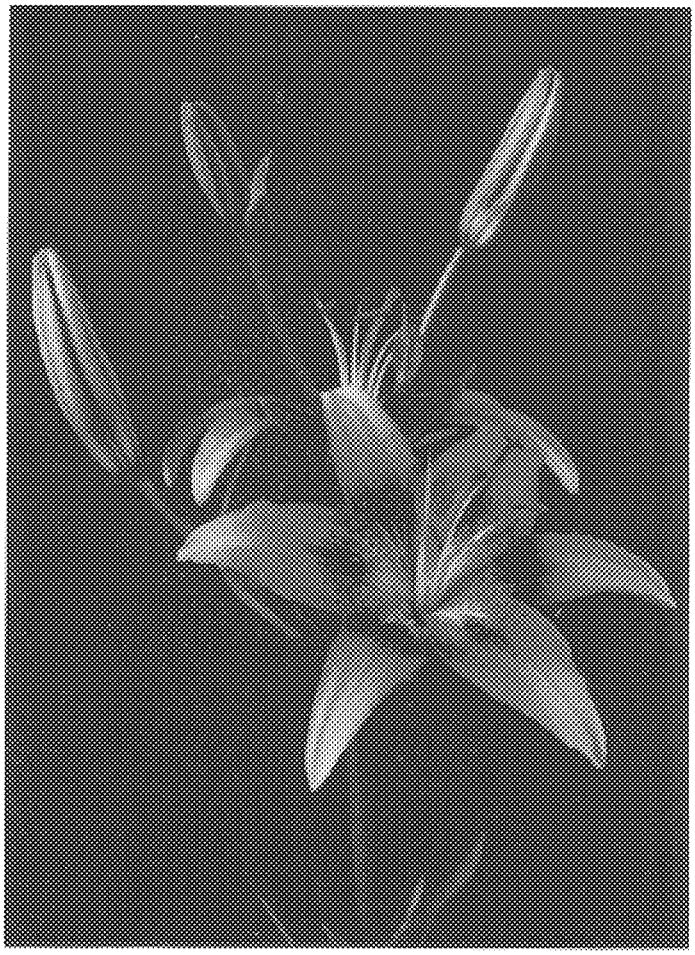
FIG 2. is a photograph showing typical flower and vegetative characteristics of 'Pink Pagado'.

The photographs of the drawing were taken in September 1996 in a studio and illustrate the typical flower and foliage form, with color as true as reasonably possible in this type of color photograph.

DETAILED DESCRIPTION

The following is a detailed description of the invention based on plants produced under commercial practices in the Cebeco Lilies, Inc. fields in Hubbard, Oreg. in July 1996.

Plants grown in greenhouses or under cooler temperatures will vary. Color references are made to The Royal Horticultural Society Colour Chart, except where the context indicates a term having its ordinary dictionary meaning.

The Plant

Origin: Seedling.

Parentage:

*Seed parent.*—A-001-85, 'Tamara'.

*Pollen parent.*—A-090-82, 'Beaudacious'.

Commercial Classification: Hybrid Asiatic lily, garden type.

Classification: Division I-A, Upright Asiatic Hybrid Lily, according to The Horticultural Classification of Lilies by The Royal Horticultural Society of London.

Form: Single erect stem bearing terminal cluster of flowers.

Height: About 62 cm. from the top of the soil to the top of the flowers from bulbs of 16 cm. in circumference.

Stem color: Yellow-green. Yellow-Green Group 144A with maroon blotches.

Growth habit: Vigorous, upright and rigid.

Internode: About 5 mm.

Foliage:

*Arrangement.*—Spiral.

*Leaf size.*—To about 10 cm. long and about 1.6 cm. wide.

*Leaf shape.*—Lanceolate.

*Texture.*—Leathery.

*Aspect.*—Glossy when mature with sparse villous hairs in leaf axils.

*Color.*—Medium green on both sides, lighter on the back. Closest to Yellow-Green Green Group 147A.

Bulbs:

*Size.*—Variable, ranging to about 12 to 14 cm. in circumference as used commercially.

*Color.*—White.

The Bud

Size: To about 65 mm. long and 22 mm. wide just prior to opening.

Shape: Ovoid with an obtuse tip.

Rate Of Opening: The mature bud opens slowly in response to light.

Color: Pink and Red-Purple. Pink (181D) on either side of the yellow-green (144B) midrib and maroon (187C) near the base.

The Flower

Blooming habit: Annually, once and mid season, early when field grown in the Pacific Northwest.

Days to bloom : Flowers approximately 74 days after spring greenhouse planting under typical commercial flower forcing conditions of 15 degrees Celsius night time temperatures.

Inflorescence size: About 19 cm. high and 24 cm. wide when there are eight flowers present.

Flower size: Medium.

*Diameter.—To about* 14 cm.

*Depth.*—About 3 cm.

Borne: In a modified raceme of eight flowers from bulbs 16 cm. in circumference.

Shape: When the flower first opens it is shallow bowl shape. Later the bowl flattens out.

Tepalage:

*Number.*—Six.

*Arrangement.*—Imbricated.

*Shape.*—Ovate.

*Texture. Spongy, waxy.*

*Aspect.*—Satiny.

*Size.*—Length: About 73 mm. Width: Inner tepals — about 35 mm. Outer tepals — about 26 mm. Depth of imbrication: About 8 mm.

*Nectary.*—About 24 mm. long; light yellow orange 23D.

*Projections.*—Present on either side of the nectary, as linear segments terminating in spots.

*Spots.*—On bottom one-third of tepal, except the claw. Greyed-Purple Group 187A.

*Color.*—Tepals start out at the very tip a light orange, 25B. The top one-third is a dull orange pink, Red 37 B-C, becoming more and more red-purple to 60A, with dark red-purple, 59A, and almost black, 187A brushmarks. On the inner tepals the brushmarks go up the sides of the main vein forming two bands about 2 cm. long to the nectary. At the top of the nectary the color changes to creamy orange, 23D, forming a light eye. Bottomside: Red-Purple 59B except along midrib and tip where it is 51D.

*Discoloration.*—Pinks turn more purple, the tip lightens to more light orange, and the light orange eye lightens to 20D.

*Fragrance.*—None.

Pedicel:

*Length.*—About 6 to 11 cm.

*Color.*—Yellow-green 144A with maroon blotches 187A making it dark looking.

*Orientation.*—Ascending upwardly to about 50 degrees from the horizontal.

The Reproductive Organs

Stamens:

*Number.*—Six, typical of the genus Lilium.

*Anthers before dehiscence.*—Size: About 21 mm. Color: Red-brown. Greyed-Red 178B.

*Filaments.*—Length: About 52 mm. Color: Light red-purple, Red-Purple Group 59D to white at base.

*Pollen.*—Color: Orange. Orange-Red Group 30B.

Pistil:

*Number.*—One.

*Style.*—Length: About 38 mm. Color: Orange-red-purple. Closest to Greyed-Red Group 181C.

*Stigma.*—Color: Greyed-Purple Group 187A.

The Fruit

Fertility: Fertile.

Shape: Ovoid.

Color at maturity: Soft brown.

We claim:

1. A new and distinct cultivar of Asiatic hybrid lily plant substantially as herein shown and described.

* * * * *